United States Patent
Omae et al.

(10) Patent No.: US 9,436,817 B2
(45) Date of Patent: Sep. 6, 2016

(54) INFORMATION-PROCESSING DEVICE, SERVICE-PROVIDING SYSTEM, SERVICE-PROVIDING METHOD, AND COMPUTER PROGRAM

(71) Applicant: NTT DOCOMO, INC., Tokyo (JP)

(72) Inventors: Koji Omae, Tokyo (JP); Yasutaka Sakon, Tokyo (JP); Kiyotaka Hori, Tokyo (JP); Kazuhiro Takagi, Tokyo (JP)

(73) Assignee: NTT DOCOMO, INC., Tokyo (JP)

(*) Notice: Subject to any disclaimer, the term of this patent is extended or adjusted under 35 U.S.C. 154(b) by 0 days.

(21) Appl. No.: 14/362,713

(22) PCT Filed: Feb. 20, 2013

(86) PCT No.: PCT/JP2013/054168
§ 371 (c)(1),
(2) Date: Jun. 4, 2014

(87) PCT Pub. No.: WO2013/125577
PCT Pub. Date: Aug. 29, 2013

(65) Prior Publication Data
US 2015/0007281 A1    Jan. 1, 2015

(30) Foreign Application Priority Data

Feb. 24, 2012   (JP) ................. 2012-038872

(51) Int. Cl.
| | | |
|---|---|---|
| G06F 21/60 | (2013.01) | |
| G06F 21/32 | (2013.01) | |
| H04L 9/32 | (2006.01) | |
| G06F 21/62 | (2013.01) | |
| G06F 11/14 | (2006.01) | |
| G06F 19/00 | (2011.01) | |
| H04L 29/08 | (2006.01) | |

(52) U.S. Cl.
CPC ............ *G06F 21/32* (2013.01); *G06F 11/1464* (2013.01); *G06F 19/322* (2013.01); *G06F 21/6254* (2013.01); *H04L 9/3226* (2013.01); *H04L 9/3231* (2013.01); *H04L 67/34* (2013.01)

(58) Field of Classification Search
CPC ....................................................... G06F 21/60
USPC .............................................................. 726/5
See application file for complete search history.

(56) References Cited

U.S. PATENT DOCUMENTS

| | | | | |
|---|---|---|---|---|
| 7,711,580 B1 * | 5/2010 | Hudson | ................. | G06F 19/322 434/322 |
| 2002/0010679 A1 * | 1/2002 | Felsher | ................. | G06F 19/322 705/51 |

(Continued)

FOREIGN PATENT DOCUMENTS

| | | |
|---|---|---|
| JP | 2006520967 | 9/2006 |
| JP | 2010079795 A | 4/2010 |

(Continued)

OTHER PUBLICATIONS

PCT International Search Report issued in International Application No. PCT/JP2013/054168, date mailed Apr. 2, 2013, pp. 1-2.

(Continued)

*Primary Examiner* — William Powers
(74) *Attorney, Agent, or Firm* — MKG, LLC (57) ABSTRACT

Information-processing device transmits biological information not being encrypted in association with an application ID to information delivery server device, and transmits encrypted biological information in association with a user ID to backup server device. Advisory terminal accepts an input of advice according to a user data set stored in information delivery server device. Client terminal downloads the advice according to the user data set from information delivery server device.

7 Claims, 7 Drawing Sheets

(56) References Cited

U.S. PATENT DOCUMENTS

2005/0283621 A1* 12/2005 Sato .................. G06F 21/6254
 713/189
2006/0083207 A1  4/2006 Karimi et al.
2012/0137343 A1* 5/2012 Uchida .............. G06F 21/6245
 726/1

FOREIGN PATENT DOCUMENTS

| | | |
|---|---|---|
| JP | 2011027917 A | 2/2011 |
| WO | 2010076840 A1 | 7/2010 |
| WO | 2011018937 A1 | 2/2011 |

OTHER PUBLICATIONS

Notice of Reasons for Rejection issued in corresponding JP Application No. 2012-038872, mailed Aug. 13, 2013, pp. 1-3.
Extended European Search Report for European Patent Application No. 13751784.3-1853/2819056, PCT/JP2013054168, dated Sep. 28, 2015.
Begemann, Ole, "How to Replace the UDID", retrieved from the internet: URL:https://web.archive.org/web/20111011145610/http://oleb.net/blog/2011/09/how-to-replace-the-udid/, dated Sep. 28, 2011.
First Notification of Office Action for Chinese Patent Application No. 201380004193.1, dated Jan. 12, 2016.

* cited by examiner

| APPLICATION ID : 000000001 | | | | |
|---|---|---|---|---|
| MEASUREMENT DATE | WEIGHT (kg) | BLOOD PRESSURE (mmHg) | STEPS (STEPS) | ADVICE |
| 2012/1/10 | 68.6 | 88-122 | 2567 | |
| 2012/1/11 | 68.4 | 78-120 | 3424 | |
| 2012/1/12 | 68.8 | 69-114 | 10243 | |
| 2012/1/13 | 67.9 | 68-108 | 11586 | |
| ... | ... | ... | ... | ... |

| MEASUREMENT DATE | WEIGHT (kg) | BLOOD PRESSURE (mmHg) | STEPS (STEPS) | ADVICE |
|---|---|---|---|---|
| 2012/1/10 | 68.6 | 88-122 | 2567 | THE WEIGHT INCREASES FROM LAST MONTH ·· |
| 2012/1/11 | 68.4 | 78-120 | 3424 | WALKING IS ·· |
| 2012/1/12 | 68.8 | 69-114 | 10243 | YOU EXERCISED ADEQUATELY ·· |
| 2012/1/13 | 67.9 | 68-108 | 11586 | FOR REVERSAL OF HYPOTENSION ·· |
| ... | ... | ... | ... | ... |

| USER ID:000000001 | | | | |
|---|---|---|---|---|
| MEASUREMENT DATE | WEIGHT (kg) | BLOOD PRESSURE (mmHg) | STEPS (STEPS) | ADVICE |
| * * * * * | * * * | * * * * * | * * * * * | * * * * * * * * * |
| * * * * * | * * * | * * * * * | * * * * * | * * * * * * * * * |
| * * * * * | * * * | * * * * * | * * * * * | * * * * * * * * * |
| * * * * * | * * * | * * * * * | * * * * * | * * * * * * * * * |
| ... | ... | ... | ... | ... |

INFORMATION-PROCESSING DEVICE, SERVICE-PROVIDING SYSTEM, SERVICE-PROVIDING METHOD, AND COMPUTER PROGRAM

TECHNICAL FIELD

The present invention relates to a technique for providing a service by which personal information is protected.

BACKGROUND ART

Heretofore, in systems providing services to users via a network, various techniques have been used to ensure confidentiality of data that is transmitted and/or received, and also security of user certification. For example, it is disclosed in JP2011-27917A that after carrying out certification using certification information such as user IDs, a client terminal transmits encrypted data to a server device, and the server device stores the encrypted data. Furthermore, in JP2010-79795A it is disclosed that by assigning a unique application ID to each of an application being delivered to a client terminal, application IDs can be used for certifying applications.

SUMMARY OF THE INVENTION

In a case when a service provider using a system disclosed in one of the above-mentioned documents or the like is a medical service provider, and so on, data sets about users (hereinafter referred to as user data sets) handled by a system may include a large amount of personal information such as information about a human body (health state), and so on, in addition to a name and an age. Therefore, it is important to maintain confidential such data sets. Thus, in a case that user data sets can be accessed by a third person including the service provider, it is not desirable for the data sets to be linked with any other data sets that identify a user, so as to protect personal information. Furthermore, in such a system, backup of data for storage in a storage device in the system should be carried out at regular intervals. However, events such as leakage of data sets containing personal information to a third party must be avoided.

Accordingly, an object of the present invention is to prevent a service provider from identifying a user who receives a service uniquely when the service is provided based on a user data set, as well as, when storing user data sets in a device other than an information-processing device that belongs to a user, to prevent contents of a user data set that is linked to the user from being identified, even if the user data set is leaked.

An information-processing device according to an embodiment of the present invention includes: a user data set obtaining unit that obtains a user data set associated with a user, the user data set not including information identifying the user personally; a user identifier obtaining unit that obtains a user identifier assigned to the user uniquely; an application identifier obtaining unit that obtains an application identifier identifying an application program indicating a procedure for providing a service to the user based on the user data set, the application identifier being assigned to the application program so that each application program executed in each information-processing device is uniquely identified by the application identifier; a first processing unit that transmits the user data set obtained by the user data set obtaining unit when the application program is executed and transmits the application identifier assigned to the application program executed in the information-processing device to a first server device providing the service to the user based on the user data set, receives service information associated with the service from the first server device, and outputs the service information; and a second processing unit that transmits an encrypted user data set and the user identifier obtained by the user identifier obtaining unit to a second server device storing the encrypted user data set in association with the user identifier.

In a preferred embodiment, the second processing unit transmits a request for the encrypted user data set to the second server device by notifying the user identifier to the second server device, receives the encrypted user data set transmitted from the second server device in response to the request, and decrypts the received encrypted user data set.

In another preferred embodiment, when a plurality of services are provided by one or a plurality of first server devices, the first processing unit, in connection with each of said one or the plurality of first server devices providing each of the plurality of services, transmits to the first server device the user data set obtained when the application program indicating the procedure for providing the service to the user is executed and the application identifier assigned to the application program is executed in the information-processing device, and receives the service information associated with the service from the first server device; and the second processing unit encrypts each of user data sets obtained by the user data obtaining unit when each of a plurality of application programs for providing each of the plurality of services is executed, and transmits all of the encrypted user data sets at once in association with the user identifier.

In another preferred embodiment, each of the application programs is stored in the first server device, the application identifier obtaining unit obtains the application identifier uniquely assigned to an application program executed in the information-processing device from the first server device by use of a web browser compliant with Hyper Text Markup Language 5 (HTML5), and the first processing unit and the second processing unit carry out data communication with the first server device and the second server device by use of the web browser.

According to an embodiment of the present invention a service-providing system includes: a plurality of information-processing devices; an input terminal; a first server device that provides a service to a user based on a user data set associated with the user, the user data set not including information identifying the user personally; and a second server device that stores the user data set encrypted in association with a user identifier assigned to the user, wherein each information-processing device comprises: a user data set obtaining unit that obtains a user data set associated with a user of the information-processing device, the user data set not including information identifying the user of the information-processing device personally; a user identifier obtaining unit that obtains a user identifier assigned to the user uniquely; an application identifier obtaining unit that obtains an application identifier to identify an application program indicating a procedure for providing a service to the user based on the user data set, the application identifier being assigned to the application program so that each application program executed in each information-processing device is uniquely identified by the application identifier; a first processing unit that transmits, when the application program is executed, the user data set obtained by the user data set obtaining unit and the application identifier assigned to the application program executed in the information-processing device to the first server device, and receives service information associated with the service from the first server device, and outputs the service information; and a second processing unit that transmits an encrypted user data set and the user identifier obtained by the user identifier obtaining unit to the second server device, requests the encrypted user data set to the second server device by notifying the user identifier, receives the encrypted user data set transmitted from the second server device in response to the request, and decrypts the received encrypted data set; the input terminal comprising: a display unit that displays the user data set stored in the first server device; and an operation unit that accepts an operation to input the service information and the application identifier; the first server device comprising: a first receiving unit that receives the user data set and the application identifier from the information-processing device; a first storage unit that stores the user data set received by the first receiving unit in association with the application identifier, and stores the service information input at the input device in association with the user data set corresponding to the application identifier input at the input device; and a first transmission unit that transmits the service information to the information-processing device; the second server device comprising: a second receiving unit that receives the encrypted user data set and the user identifier from the information-processing device; and a second storage unit that stores the encrypted user data set in association with the user identifier received by the second receiving unit.

A service providing method according to another embodiment of the present invention includes: a step of obtaining a user data set associated with a user, the user data set not including information identifying the user personally; a step of obtaining a user identifier assigned to the user uniquely; a step of obtaining an application identifier to identify an application program indicating a procedure for providing a service to the user based on the user data set, the application identifier being assigned to the application program so that each application program executed in each information-processing device is uniquely identified by the application identifier; a step of transmitting the user data set obtained when the application program is executed and the application identifier assigned to the application program executed in the information-processing device to a first server device providing the service to the user based on the user data set, receiving service information associated with the service from the first server device, and outputting the service information; and a step of transmitting an encrypted user data set and the obtained user identifier to a second server device storing the encrypted user data set in association with the user identifier.

A program according to another embodiment of the present invention for causing a computer to execute: a step of obtaining a user data set associated with a user, the user data set not including information identifying the user personally; a step of obtaining a user identifier assigned to the user uniquely; a step of obtaining an application identifier to identify an application program indicating a procedure for providing a service to the user based on the user data set, the application identifier being assigned to the application program so that each application program executed in each information-processing device is uniquely identified by the application identifier; a step of transmitting the user data set obtained when the application program is executed and the application identifier assigned to the application program executed in the information-processing device to a first server device providing the service to the user based on the user data set, receiving service information associated with the service from the first server device, and outputting the service information; and a step of transmitting an encrypted user data set and the obtained user identifier to a second server device storing the encrypted user data set in association with the user identifier According to the present invention, it is possible to prevent a service provider from identifying a user who receives a service uniquely when the service is provided based on a user data set, and, when storing user data sets in a device, which is different from an information-processing device that belongs to a user, contents of a user data set that is linked to prevent identification of the user, even if the user data set is leaked.

DETAILED DESCRIPTION

Figure 1:
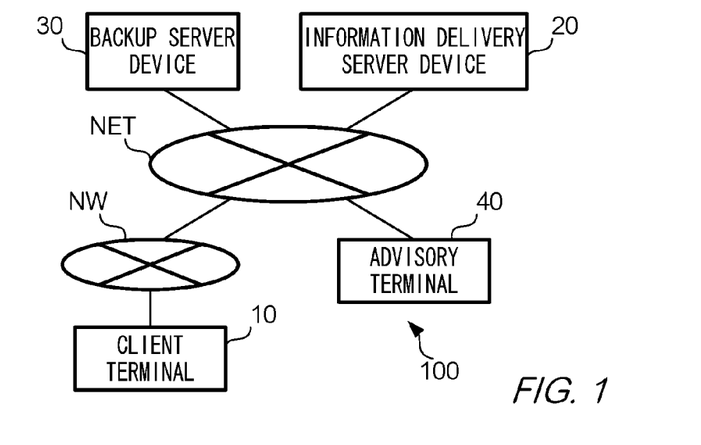
FIG. 1 is a block diagram showing a configuration of a service-providing system according to an embodiment.

FIG. 1 is a block diagram showing a system configuration of service-providing system 100 according to an embodiment. Service-providing system 100 is made up of client terminal 10, information delivery server device 20, backup server device 30, advisory terminal 40, mobile communication network NW, and Internet NET. There may be plural client terminals 10 and plural advisory terminals 40. Client terminal 10 is an example of an information-processing device. Information delivery server device 20 is an example of a first server device. Backup server device 30 is an example of a second server device. Advisory terminal 40 is an example of an input terminal. Mobile communication network NW is a mobile communication network including, for example, a cellular phone network or an intercommunication network such as a wireless LAN (Local Area Network). Internet NET is a fixed communication network provided by telecommunications carriers.

Client terminal 10 connects with mobile communication network NW and communicates with information delivery server device 20 and backup server device 30 mutually via Internet NET. Furthermore, advisory terminal 40 communicates with information delivery server device 20 mutually via Internet NET. Service-providing system 100 provides appropriate service for each user of the system based on data input by each user using client terminal 10. In the present embodiment, as an example of service-providing system 100, a case that a service provider is a health club is described as an example. Specifically, the service provider in the present embodiment is a corporation that is an operator of the health club. An adviser, who is an employee of the health club, provides a service of inputting appropriate advice for health care to a user of the health club, by using advisory terminal 40, based on biological information regarding a user's body (hereinafter called biological information) such as weight or blood pressure input by the user using client terminal 10. Biological information is an example of a user data set that is a data set regarding a user. The advice provided to a user is an example of service information.

Client terminal 10 is a terminal used by a user of service-providing system 100. Client terminal 10 is a communication terminal that can communicate with information delivery server device 20 and backup server device 30, such as a mobile phone, a wireless terminal being accessible to wireless LAN, a PC (Personal Computer) with wired or wireless communication facility or a car navigation system. A mobile phone shown in FIG. 1 is an example of client terminal 10. Information delivery server device 20 is a computer that stores biological information of a user transmitted from client terminal 10 and stores advice input from advisory terminal 40 in association with the biological information of a user. Backup server device 30 is a computer that stores biological information of a user transmitted from client terminal 10 as backup data. Advisory terminal 40 is a computer used when an adviser of the health club inputs advice. Advisory terminal 40 is a terminal such as a mobile phone or a PC; in the present embodiment, a PC is used as an example of advisory terminal 40.

A manager of information delivery server device 20 and backup server device 30 is, for example, a person who performs the duty of a carrier that provides a communication service via mobile telephone network included in network NW commercially. An adviser, who is an employee of the health club that is the service provider, can input advice by using advisory terminal 40, and s/he is not required to manage information delivery server device 20 and backup server device 30, manually.

To receive the service, at first, a user makes a contract in writing, with the health club that is the service provider, via the Internet, and so on, regarding use of the service. Then, the carrier managing information delivery server device 20 and backup server device 30 publishes a pair of a user ID and a user password, and notifies the service provider thereof. In addition, the carrier conducts setting at backup server device 30 for admitting a user of the user ID included in the notification to use of the service. Next, the service provider mails the pair of the user ID and the password to the user to be used as certification information when using the service.

The user may receive them by means other than postal mail; for example, as an electronic message such as email. Client terminal 10 logs in to backup server device 30 using the received certification information based on an operation performed by the user, and transmits a download request of an application program for receiving the service (hereinafter, merely referred to as an application). Backup server device 30 authenticates the received certification information. When the process for admitting a user to use the service has been conducted for the user ID included in the received certification information, the certification is completed successfully, and the request to download an application is accepted. Since each user ID is unique, it cannot be avoided that an employee of the service provider can know users' personal information, such as their names, if a search is conducted by use of user IDs as search keys in a user profile database that the service provider generally maintains for user management. Namely, a user ID is information that can identify an individual user uniquely. The user ID is an example of a user identifier.

The user allows client terminal 10 to download an application to receive the service through a website prepared by the service provider. The website is built, for example, in backup server device 30. The application described in the present embodiment is a procedure to manage biological information of the user, and hereinafter is referred to as a health management application. An identifier to distinguish each of the applications uniquely (hereinafter called an application ID) is included in the application. Client terminal 10 transmits the biological information with the application ID to information delivery server device 20, and information delivery server device 20 stores the received biological information in association with the application ID. The application ID is renumbered each time the application is downloaded; therefore, all applications, in one client terminal 10 or in several client terminals 10, have unique application IDs. The application ID is merely an identifier distinguishing an application uniquely, and is not information that can identify an individual user uniquely, such as a user ID. This is because there is no database that stores an application ID in association with a user's name in service-providing system 100. The application ID is an example of an application identifier.

When a user inputs biological information using client terminal 10, client terminal 10 communicates with information delivery server device 20 using the application ID and transmits the biological information without encrypting it. On the other hand, client terminal 10 transmits encrypted biological information with the user ID to backup server device 30 after certification using a user ID as certification information. In other words, biological information stored in information delivery server device 20 is not associated with information that can identify an individual user uniquely, but only backup data of the encrypted biological information stored in backup server device 30 is associated with information that can identify an individual user uniquely. Because client terminal 10 is the only device storing the user ID in association with the application ID, the biological information and information that can identify an individual user are not linked at any device except client terminal 30. Therefore, a service provider cannot identify which user the biological information relates to.

Figure 2:
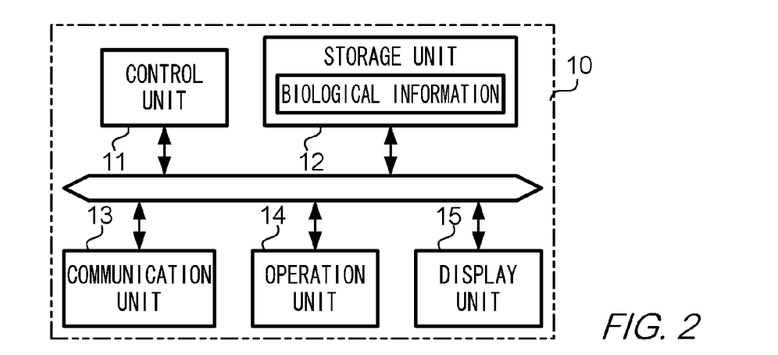
FIG. 2 is a block diagram showing a hardware configuration of a client device.

FIG. 2 is a block diagram showing a hardware configuration of client terminal 10. Client terminal 10 includes control unit 11, storage unit 12, communication unit 13, operation unit 14 and display unit 15, and the parts are interconnected via a bus. Control unit 11 includes a CPU (Central Processing Unit), a RAM (Random Access Memory) and a ROM (Read Only Memory). The CPU controls each part of client terminal 10 by reading programs stored in the ROM and/or storage unit 12, loading them into the RAM, and executing them.

Storage unit 12 is a non-volatile storage means such as EEPROM (Electrically Erasable and Programmable ROM) and flash memory. Storage unit 12 stores various programs and thresholds, and also stores biological information input by a user. Communication unit 13 connects with mobile communication network NW and communicates with information server device 20 and backup server device 30 via Internet NET under control of control unit 11. Operation unit 14 includes plural keys, and supplies a signal in accordance with content of operation to control unit 11 when a user operates these keys. Control unit 11 determines content of the operation based on the signal and executes processing. The user inputs his/her biological information using operation unit 14. Display unit 15 includes a display device such as a liquid crystal display and a memory such as VRAM (Video Random Access Memory), and displays various images under the control of control unit 11.

Figure 3:
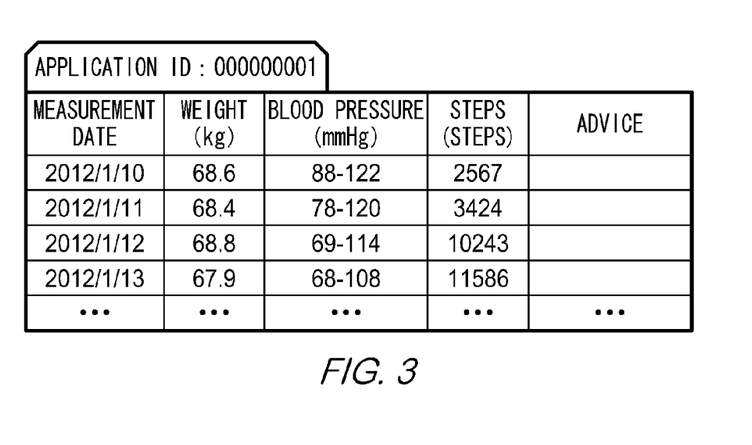
FIG. 3 is a diagram representing an example of biological information stored in the client terminal.

FIG. 3 is a diagram representing an example of biological information stored in client terminal 10. The biological information includes a measurement date, weight, blood pressure, a number of steps taken, and advice. The measurement date is a date when the user measured his/her biological information. The biological information includes weight, blood pressure and a number of steps taken, measured by the user with respect to each measurement date. The information described above is only an example, and blood sugar level, body fat percentage, and so on may be included in the information. The advice is an item where content of advice input by the adviser is described, and the item is blank if no advice is obtained from the adviser. The biological information is stored in storage unit 12 in association with an application ID. This application ID is equal to an application ID included in the health management application downloaded to client terminal 10.

Figure 4:
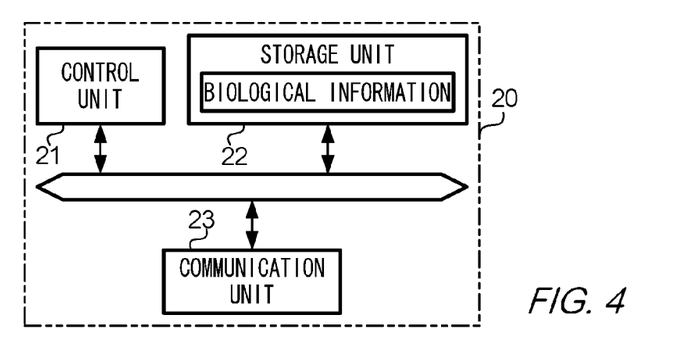
FIG. 4 is a block diagram showing a hardware configuration of an information delivery server device.

FIG. 4 is a block diagram showing a hardware configuration of information delivery server device 20. Information delivery server device 20 includes control unit 21, storage unit 22, and communication unit 23, and the parts are interconnected via a bus. Control unit 21 includes a CPU, a RAM, and a ROM. The CPU controls each part of information delivery server device 20 by reading programs stored in the ROM and/or storage unit 22, loading them into the RAM, and executing them. Storage unit 22 is storage means such as a hard disk. Storage unit 22 stores various programs and thresholds, and also stores biological information transmitted from client terminal 10. Communication unit 23 communicates with client terminal 10 and advisory terminal 40 via Internet NET under the control of control unit 21. Storage unit 22 is an example of a first storage unit. Also, control unit 21 and communication unit 23 collaborate to realize a first receiving unit and a first transmitting unit.

Figure 5:
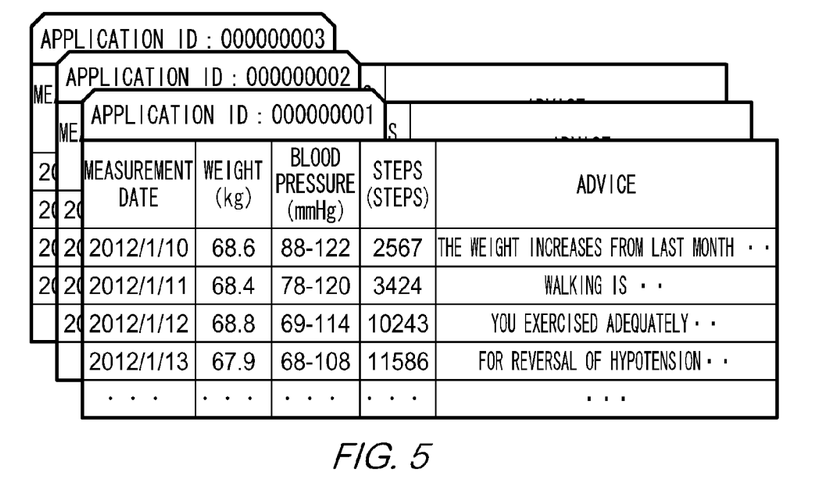
FIG. 5 is a diagram representing an example of biological information stored in the information delivery server device.

FIG. 5 is a diagram representing an example of biological information stored in information delivery server device 20. Content of the biological information is equal to the content of the biological information stored in client terminal 10. FIG. 5 shows the biological information after input of advice by the adviser using advisory terminal 40. The advice input by the adviser relates to the biological information of the user of each measurement date for health management. The biological information stored in information delivery server device 20 is associated with an application ID. The application ID is an application ID of the health management application used when client terminal 10 transmits biological information to information delivery server device 20. When the biological information is transmitted from client terminal 10, information delivery server device 20 receives and stores the biological information in association with the application ID used during the communication.

Figure 6:
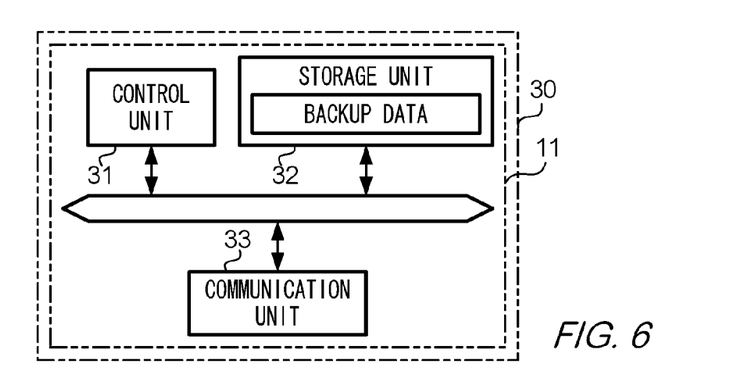
FIG. 6 is a block diagram showing a hardware configuration of a server device for backup.

FIG. 6 is a block diagram showing a hardware configuration of backup server device 30. Backup server device 30 includes control unit 31, storage unit 32 and communication unit 33, and the units are interconnected via a bus. Control unit 31 includes a CPU, a RAM, and a ROM. The CPU controls each unit of backup server device 30 by reading programs stored in the ROM and/or storage unit 32, loading them into the RAM and executing them. Communication unit 33 communicates with client terminal 10 via Internet NET under the control of control unit 31. Storage unit 32 is a storage means such as a hard disk. Storage unit 32 stores various programs and thresholds, together with a list of certification information. Furthermore, storage unit 32 stores the encrypted biological information transmitted from client terminal 10 as backup data. The list of the certification information is a group of sets of a user ID and a password assigned to each user. Storage unit 32 is an example of a second storage unit. Also, control unit 31 and communication unit 33 collaborate to realize a second transmitting unit.

Figure 7:
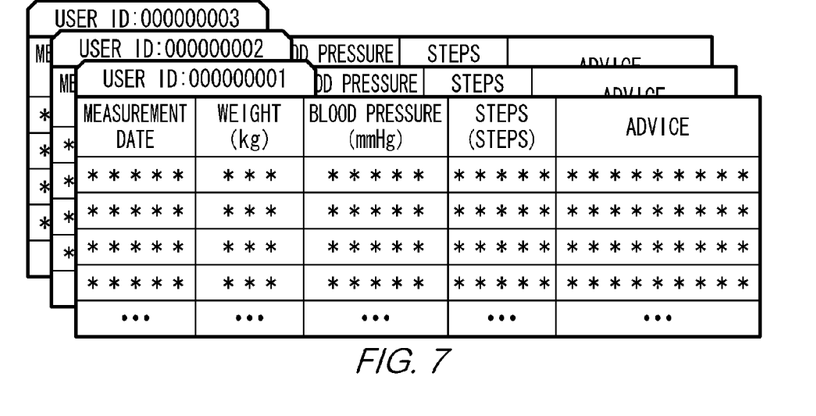
FIG. 7 is a diagram representing an example of backup data.

FIG. 7 is a diagram representing an example of backup data. The content of the biological information stored as the backup data is equal to the content of the biological information stored in client terminal 10 and information delivery server device 20. The biological information is associated with the user ID in the backup data. The biological information is encrypted; however, the user ID is not encrypted because the user ID is not equal to biological information. The user ID shown in FIG. 7 is the user ID used during the certification for backup server device 30 by client terminal 10. In other words, the user ID is the user ID added to the encrypted biological information by client terminal 10 when the encrypted biological information is transmitted.

Figure 8:
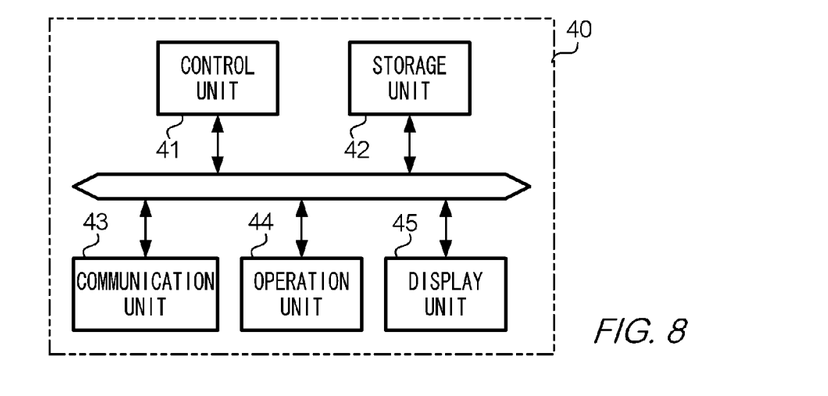
FIG. 8 is a block diagram showing a hardware configuration of an adviser device.

FIG. 8 is a block diagram showing a hardware configuration of advisory terminal 40. Advisory terminal 40 includes control unit 41, storage unit 42, communication unit 43, operation unit 44, and display unit 45, and the units are interconnected via a bus. Control unit 41 includes a CPU, a RAM, and a ROM. The CPU controls each part of advisory terminal 40 by reading programs stored in the ROM and/or storage unit 42, loading them into the RAM, and executing them. Storage unit 42 is a storage means such as a hard disk, and stores various programs. Communication unit 43 communicates with information delivery server device 20 via Internet NET under the control of control unit 41. Operation unit 44 includes plural keys, and supplies a signal in accordance with content of operation to control unit 41 when the adviser operates these keys. Control unit 41 determines content of the operation based on the signal and executes processing. The adviser inputs advice relating to the biological information of the user using operation unit 44. Display unit 45 includes a display device such as a liquid crystal display and a memory such as VRAM, and displays various images under the control of control unit 41.

Figure 9:
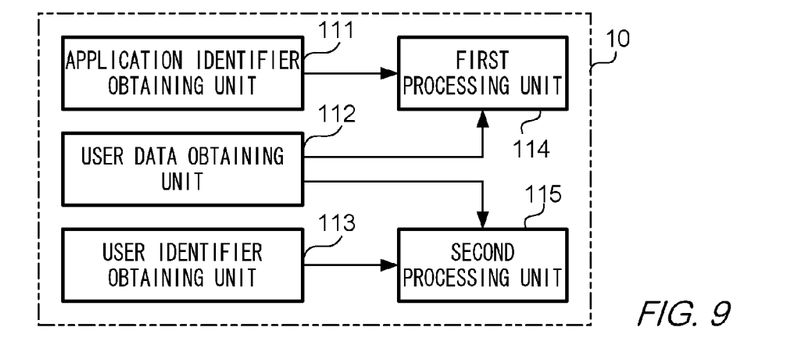
FIG. 9 is a block diagram showing a functional configuration of a control unit of the client terminal.

FIG. 9 is a block diagram showing a functional configuration of control unit 11 of client terminal 10.

Application identifier obtaining unit 111 obtains an application identifier assigned to the application program at which a procedure to provide a service to a user based on the user data is described. User data obtaining unit 112 obtains user data, which is data relating to a user. User identifier obtaining unit 113 obtains a user identifier assigned to a user.

When the application program is executed, first processing unit 114 transmits the user data obtained by user data obtaining unit 112, in association with the application identifier assigned to an application program, to the first server device providing a service to a user based on the user data. Furthermore, first processing unit 114 receives and outputs service information related to the service when the service information is transmitted from the first server device. Second processing unit 115 transmits encrypted user data in association with the user identifier obtained by the user identifier obtaining unit 113 to a second server device storing the encrypted user data in association with the user identifier.

Operation of service-providing system 100 will now be described.

Figure 10:
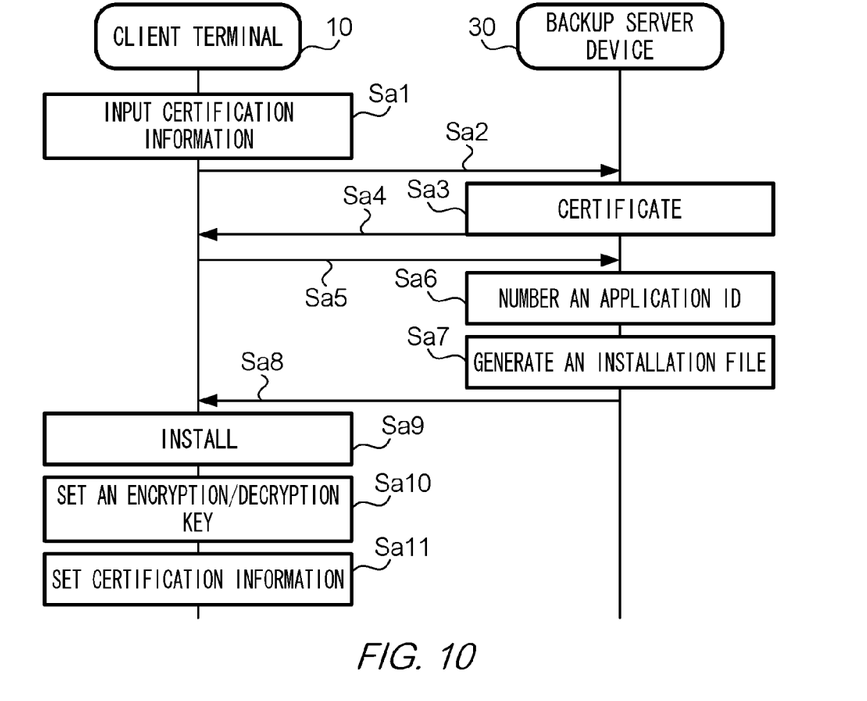
FIG. 10 is a sequence diagram showing processing of downloading an application.

FIG. 10 is a sequence diagram showing processing of downloading an application. It is assumed here that a user has already made an agreement with a service provider regarding a use of a service, and received a set of a user ID and a password as certification information in writing or by email.

First, control unit 10 accepts an input of certification information when the user inputs the certification information to client terminal 10 using operation unit 14 (step Sa1). Next, control unit 11 of client terminal 10 transmits the input certification information to backup server device 30 using communication unit 13 (step Sa2). Upon receiving the certification information using communication unit 33, control unit 31 of backup server device 30 stores the received certification information in correspondence with the list of certification information stored in storage unit 32 and certifies the user (step Sa3). Control unit 31 of backup server device 30 transmits a result of the certification using communication unit 33 (step Sa4). In the following description, a case when the certification is completed successfully is described. When the certification is completed successfully, control unit 11 of client terminal 10 transmits a request to download the health management application, using communication unit 13, to backup server device 30 (step Sa5). Control unit 31 of backup server device 30 numbers an application ID when receiving the request using communication unit 33 (step Sa6). Storage unit 32 of backup server device 30 stores a numbered application ID table listing the numbered application IDs. Control unit 31 numbers an ID that is not stored in the numbered application ID table as a new application ID, and stores the new numbered application ID in storage unit 32 by adding the numbered application ID to the numbered application ID table.

Next, control unit 31 sets the application ID numbered at step Sa6, an identifier to identify uniquely information delivery server device 20 that is a destination device of the biological information, and an identifier to identify uniquely backup server device 30 that is a destination device of the biological information, to store in program files of the application as parameters. Furthermore, control unit 31 generates an installation file of the application including the program files (step Sa7). The identifiers that identify information delivery server device 20 and backup server device 30 are, for example, URLs (Uniform Resource Locaters). Control unit 31 transmits the generated installation file to client terminal 10 using communication unit 33 (step Sa8).

Upon receiving the installation file using communication unit 13, control unit 11 of client terminal 10 expands it in the RAM based on an instruction input by a user of operation unit 14, and installs the application onto client terminal 10 (step Sa9). Control unit 11 causes storage unit 12 to store the application ID and a URL included in the installation file at this time. Next, control unit 11 causes display unit 15 to display an image promoting setting of an encryption/decryption key used for encryption when transmitting the biological information to backup server device 30, and used for decryption when recovering backup data from backup server device 30. Control unit 11 accepts an input of an encryption/decryption key by a user (step Sa10). According to this embodiment, the encryption/decryption key is a string. The user inputs a string to client terminal 10 using operation unit 14, and control unit 11 of client terminal 10 stores the input string as an encryption/decryption key. This encryption/decryption key is not sent to other external terminals such as information delivery server device 20 and backup server device 30, and is information that can only be known by the user who set it and client terminal 10. The encryption/decryption key is an example of key information.

Next, control unit 11 causes display unit 15 to display an image promoting an input of the certification information, and accepts the input of the certification (step Sa11). Upon inputting of the certification information by the user of operation unit 14, control unit 11 of client terminal 10 causes storage unit 12 to store the downloaded application in association with the input certification. In this way, the user is not required to input the certification information each time the encrypted biological information is sent to backup server device 30. The foregoing description explains the process of downloading applications.

Next, the process of transmitting the biological information from client terminal 10 to information delivery server device 20 and backup server device 30 will be described.

Figure 11:
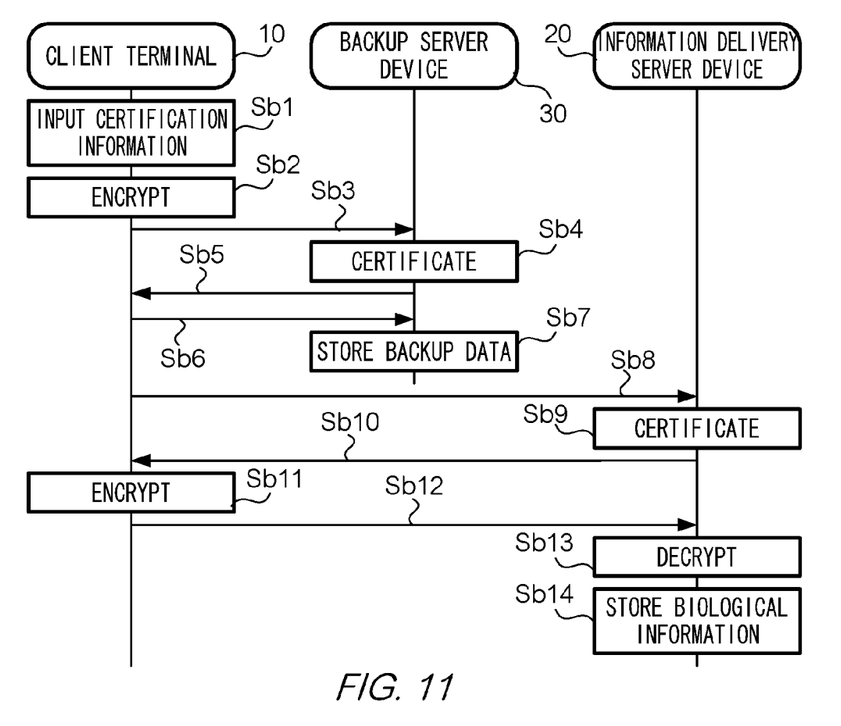
FIG. 11 is a sequence diagram showing processing of transmitting biological information to a server device.

FIG. 11 is a sequence diagram showing a process of transmitting the biological information to server device 30. First, upon user input of his/her biological information to client terminal 10 using operation unit 14, control unit 11 accepts the input of the biological information (step Sb1). Next, control unit 11 of client terminal 10 encrypts the input biological information using the encryption/decryption key that is set at step Sa10 and stored in storage unit 12, and causes it to be stored in storage unit 12 (step Sb2). At this step, the biological information is encrypted and the application ID is not encrypted.

Next, control unit 11 of client terminal 10 causes communication unit 13 to transmit the certification information stored in storage unit 12 to backup server device 30 (step Sb3). Upon receiving the certification information via communication unit 33, control unit 31 of backup server device 30 certifies the user by storing the received certification information in correspondence with the list of the certification information stored in storage unit 32 (step Sb4). Control unit 31 of backup server device 30 transmits a result of the certification to client terminal 10 using communication unit 33 (step Sb5). In the following description, a case when the certification is completed successfully is described. Upon the certification being completed successfully, control unit 11 transmits the encrypted biological information in association with the user ID to backup server device 30 via communication unit 13 (step Sb6). Upon receiving the information via communication unit 33, control unit 31 of backup server device 30 causes storage unit 32 to store the received encrypted biological information in association with the received user ID as backup data (step Sb7). According to this embodiment, "transmitting one item of information in association with another item of information" means "transmitting both items of information in one data transmission," and "receiving one item of information in association with another item of information" means "receiving both items of information in one received data transmission." These expressions have the same meanings in the following description.

Next, control unit 11 of client terminal 10 transmits the application ID corresponding to the biological information stored in storage unit 12, while setting the application ID as a parameter of a URL, using communication unit 13 (step Sb8). Control unit 21 of information delivery server device 20 certifies the user by storing the received application ID in correspondence with the numbered application ID table stored in storage unit 22 (step Sb9). Control unit 21 of information delivery server device 20 transmits a result of the certification to client terminal 10 using communication unit 23 (step Sb10). In the following description, a case that of the certification being completed successfully is described. Upon the certification being completed successfully, control unit 11 encrypts the input biological information (step Sb11). For the encryption, the encryption/decryption key that could be known only by client terminal 10 and backup server device 30 described above is not used, but common encryption means such as SSL (Secure Socket Layer) is used. Control unit 11 transmits the biological information encrypted by SSL to information delivery server device 20 using communication unit 13 (step Sb12). The user ID is not added to the biological information at this step. Upon receiving the information via communication unit 23, control unit 21 of information delivery server device 20 decrypts the received biological information (step Sb13). Control unit 21 causes storage unit 22 to store the decrypted biological information in association with the received application ID (step Sb14). The foregoing description explains the process of transmitting the biological information to information delivery server device 20.

A process of an adviser inputting advice about the biological information and a user referring to the advice will now be described.

Figure 12:
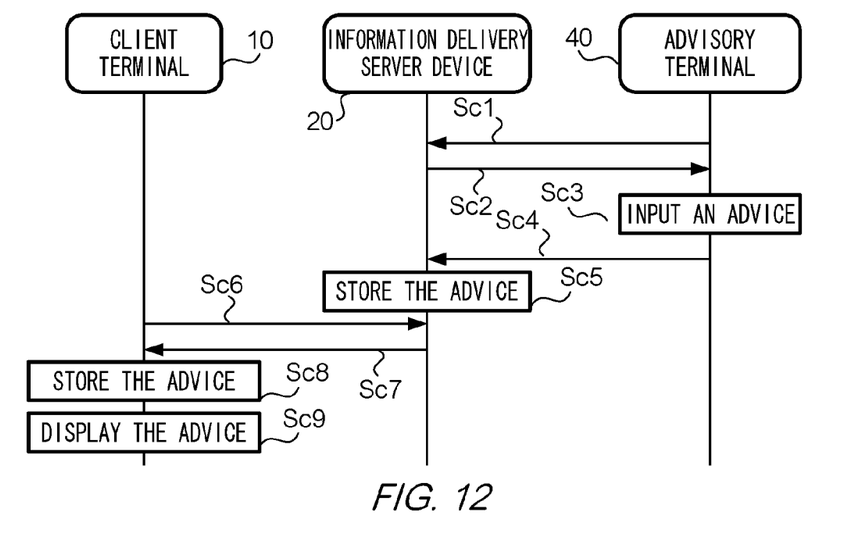
FIG. 12 is a sequence diagram showing processing of registration and reference of an advice.

FIG. 12 is a sequence diagram showing processing of registration and referring to advice. First, control unit 41 of advisory terminal 40 transmits a request for the biological information of a user to information delivery server device 20 via communication unit 43, based on an instruction input by the adviser using operation unit 44 of advisor terminal 40 (step Sc1). Upon receiving the request via communication unit 23, control unit 21 of information delivery server device 20 transmits to advisory terminal 40 the biological information of the user stored in storage unit 22 together with an application ID that is associated with the biological information via communication unit 23 (step Sc2). Upon receiving the communication via communication unit 43, control unit 41 of advisory terminal 40 causes display unit 45 to display the received biological information with respect to each received application ID, and the adviser inputs to advisory terminal 40 advice relating to the displayed biological information, via operation unit 44 (step Sc3). Display unit 45 is an example of a display unit, and operation unit 44 is an example of an operation unit. In step Sc3, the adviser cannot identify a user of the biological information from the biological information because the biological information does not correspond to the user ID, but only corresponds to the application ID. The advice is associated with the biological information by using, for example, a set of the application ID and the measurement date as a key. When the adviser completes the input of the advice, control unit 41 of advisory terminal 40 transmits the input advice, in association with the biological information that corresponds to the advice, together with the application ID that is associated with the biological information, to information delivery server device 20, via communication unit 43 (step Sc4). Upon receiving the communication via communication unit 23, control unit 21 of information delivery server device 20 causes storage unit 22 to store the received advice in association with the biological information that is associated with the received application ID (step Sc5). After step Sc5, control unit 11 of client terminal 10 transmits a request to download the advice in association with its application ID to information delivery server device 20 via communication unit 13 based on an instruction input by a user of operation unit 14 (step Sc6). Upon receiving the request via communication unit 23, control unit 21 of information delivery server device 20 transmits advice included in biological information, associated with the received application ID, from the biological information stored in storage unit 22, in association with the biological information and the received application ID, to client terminal 10, via communication unit 23 (step Sc7). Upon receiving the advice via communication unit 13, control unit 11 of client terminal 10 causes storage unit 12 to store the received advice in association with the biological information that is associated with the received application ID (step Sc8). Control unit 11 causes display unit 15 to display the biological information including the advice (step Sc9). The user can refer to the displayed advice and make use of it for his/her health care. Next, a process of data recovery using the backup data stored in backup server device 30 will be described.

Figure 13:
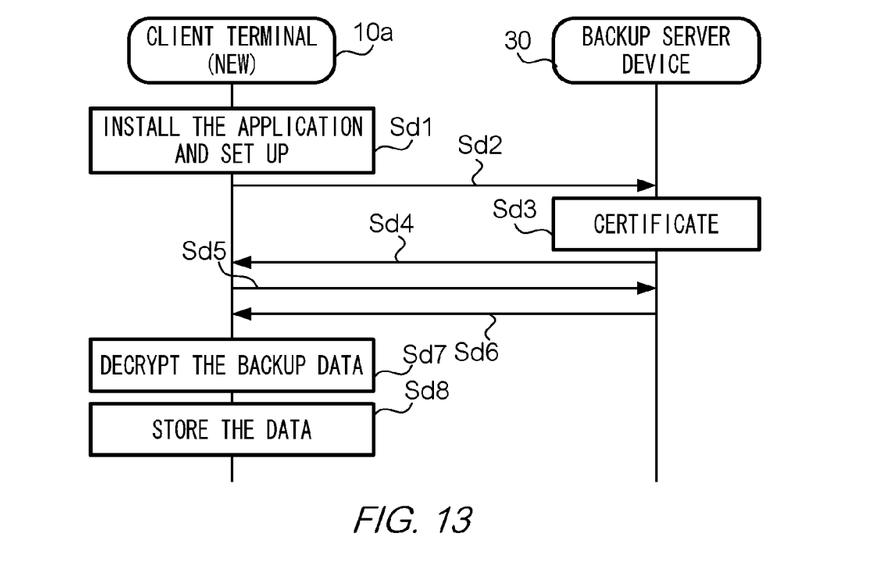
FIG. 13 is a sequence diagram showing processing of data recovery by backup data.

FIG. 13 is a sequence diagram showing a process of data recovery using the backup data.

Data recovery from the stored backup data is necessary, for example, when a user deletes data stored in storage unit 12 of client terminal 10 in error, or trades his/her client terminal 10 for a new one. In the present embodiment, a case that the user trades his/her client terminal 10 for client terminal 10a is described, as an example. Both client terminal 10 and client terminal 10a have the hardware configuration described above.

First, the user installs the application on new client terminal 10a and inputs various settings using operation unit 14 (step Sd1). The process of step Sd1 is, specifically, similar to the process shown in FIG. 10. Next, control unit 11 of client terminal 10 transmits the certification information stored in storage unit 12 to backup server device 30 via communication unit 13 (step Sd2). Upon receiving the information via communication unit 33, control unit 31 of backup server 30 certifies the user by storing the received certification information in correspondence with the list of the certification information stored in storage unit 32 (step Sd3). Control unit 31 of backup server device 30 transmits a result of the certification to client terminal 10 via communication unit 33 (step Sd4). In the following description, a case that of the certification being completed successfully is described. When the certification is completed successfully, control unit 11 transmits a request to download backup data in association with a user ID to backup server device 30 via communication unit 13 (step Sd5). Upon receiving the request via communication unit 33, control unit 31 of backup server device 30 extracts encrypted biological information associated with the received user ID from among the backup data stored in storage unit 32, and transmits the information to client terminal 10a via communication unit 33 (step Sd6). Upon receiving the information via communication unit 13, control unit 11 of client terminal 10 decrypts the received encrypted biological information using the encryption/decryption key stored in storage unit 12 (step Sd7). Control unit 11 causes storage unit 12 to store the decrypted biological information with respect to each application ID that is associated with the biological information (step Sd8).

As described above, according to the present embodiment, when the user sends the biological information to information delivery server device 20, the biological information is associated with the application ID, which cannot identify an individual uniquely, and the biological information is stored in information delivery server device 20 in such a manner that the adviser can refer to its content, as it is not encrypted. Furthermore, when the user sends the biological information for backup to backup server device 30, the biological information is associated with the user ID, which can identify an individual uniquely, and the biological information is stored in backup server device 30 in such a manner that a third party, including the adviser, cannot refer to the content of the biological information, as it is encrypted. Furthermore, the user data that the adviser can refer to is not linked with information that can identify an individual, since information that the adviser can refer to using advisor terminal 40 is only user data stored in information delivery server device 20. Therefore, the service provider cannot specify which user data belongs to which user by referring to the backup data. In addition, the key used for encryption and decryption is known only to the user who sets the key, and is stored only in client terminal 10 that belongs to the user; therefore, a personal data leak does not occur even if the contents stored in backup server device 30 are leaked.

As described above, according to the present embodiment, a service provider can be prevented from identifying a user who receives a service uniquely when the service is provided based on a user data set. Furthermore, according to the present embodiment, when storing user data sets in a device different from an information-processing device that belongs to a user, contents of a user data set that is linked to the user can be prevented from being identified, even if the user data set is leaked.

<Modification>

The present invention is not limited to the embodiment described above, but may be implemented in another embodiment. For example, the present invention may be implemented in a modified embodiment described below. It is to be noted that the present invention may be implemented in an embodiment combining plural modifications.

<Modification 1>

In the embodiment, one application is described; however, plural applications may be employed.

Figure 14:
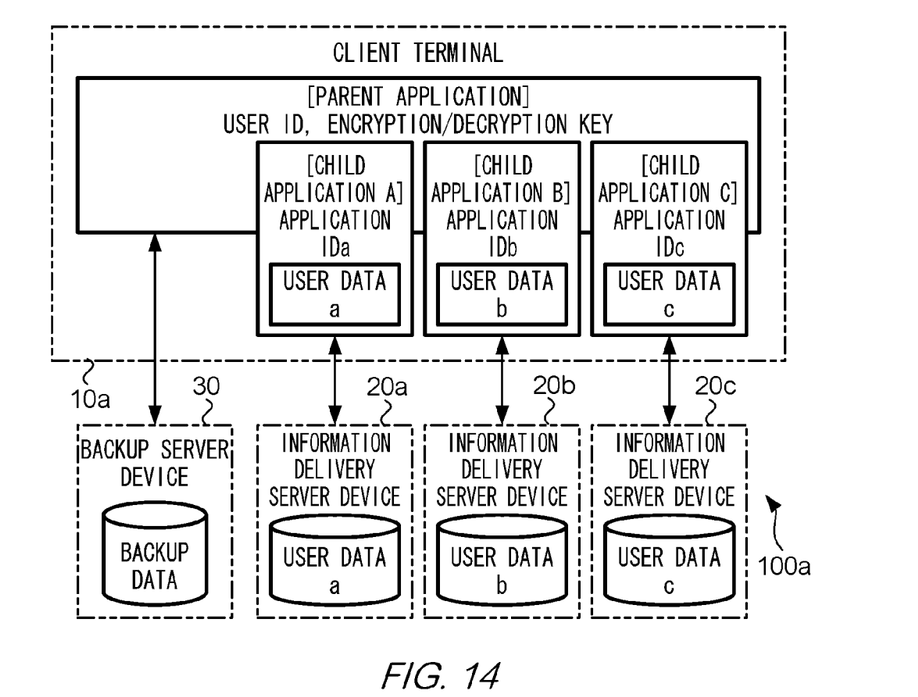
FIG. 14 is a pattern diagram schematically showing a configuration of a service-providing system of modification 1.

FIG. 14 is a pattern diagram schematically showing a configuration of service-providing system 100*a* according to modification 1. Service-providing system 100*a* is constructed by client terminal 10*a*, information delivery server device 20*a*, 20*b*, 20*c*, backup server device 30, mobile communication network NW, Internet NET and advisory terminal 40. Mobile communication network NW, Internet NET and advisory terminal 40 are the same as the ones shown in FIG. 1. It is to be noted that information delivery server device 20*a*, 20*b*, and 20*c* are referred to merely as information delivery server device 20 in a case that they are not distinguished from each other. In addition, a number of information delivery server devices 20 shown in the figure are nothing more than a single example. And, mobile communication network NW, Internet NET and advisory terminal 40 are not shown in FIG. 14 so as to explain parts that are clearly different from the ones described in the embodiment; however, client terminal 10*a* connects with mobile communication network NW and communicates with information delivery server device 20 and backup server device 30 via Internet NET, and advisory terminal 40 communicates with information delivery server device 20 via Internet NET.

Client terminal 10*a* can manage plural applications as a provision of a service for a user. Each one of the plural applications is called a child application. On the other hand, an application that manages plural child applications and backups of user data input to the child application is called a parent application. A different application ID is added to each child application. The contents of each child application are different from another, such as child application A shown in FIG. 14 is a health management application in the embodiment, child application B is a supervised administration application that manages drug status, and child application C is a dietary management application that manages content of meals. In modification 1, contents of data that a user inputs when the child application is executed are not only biological information but also other data that are different from each other, and each of the data corresponds to the user data. The user data that the user inputs according to each child application is stored in storage unit 12.

On using service-providing system 100*a*, first, the user lets client terminal 10*a* download and install the parent application from a server device that delivers applications (in the present modification, backup server device 30 is used as the server device). After letting client terminal 10*a* download the parent application, the user sets the encryption/decryption key using operation unit 14. The parent application includes the setting of encryption/decryption key. Furthermore, storage unit 12 stores a management table where the application ID of the parent application is associated with the application ID of each child application. Flags that indicate whether each child application is targeted for backup or not, are stored in the management table with respect to each child application. In a case that the state of the flag is on, the child application is a target for backup. On the other hand, in a case that the state of the flag is off, the child application is not a target for backup. The user can modify the content of the management table using operation unit 14, and can set to on only flags corresponding to child applications that the user wants to be targets for backup. And when the client terminal 10*a* downloads each child application from backup server device 30, URLs of information delivery server device 20 and backup server device 30 that are destination devices of the user data from the child applications are downloaded in association with the application ID of each child application.

In the configuration described above, for example, when the user inputs the user data to child application A using operation unit 14, control unit 11 of client terminal 10*a* communicates with information delivery server device 20*a* using communication unit 13, by appointing the URL corresponding to child application A of which the application ID is a parameter. Control unit 21 of information delivery server device 20 certifies as described above by collating the received application ID with the numbered application ID table stored in storage unit 22. Upon the certification being completed successfully, control unit 11 of client terminal 10*a* encrypts the input user data by, for example, SSL. Then, control unit 11 transmits the user data encrypted by SSL in association with the application ID of child application A (application IDa) to information delivery server device 20 using communication unit 13. Upon receiving the user data using communication unit 23, control unit 21 of information delivery server device 20 decrypts the received user data.

Then, control unit 21 lets storage unit 22 store the decrypted user data in association with the received application ID. A series of operations for the other child applications is also performed. Regarding transmission of the user data to information delivery server device 20 in Modification 1, operations are similar to those of the embodiment except that information delivery server devices 20 being destination devices of the data are different from the child applications.

On the other hand, operations for data backup in modification 1 are different from the ones of the embodiment. In modification 1, control unit 11 of client terminal 10*a* does not transmit the user data to backup server device 30 as often as transmitting the user data to information delivery server device 20. Alternatively, in modification 1, after completion of certification using the certification information, control unit 11 encrypts the user data of the target child applications in bulk using the encryption/decryption key at a predetermined timing, and transmits the encrypted user data in association with the user ID in bulk to backup server device 30. In this modification, "the target child application" means a child application, and a flag indicates whether the application is targeted for backup or not by being set to on, in the management table stored in storage unit 12. In addition, in this modification, "transmission of the user data in bulk" means that control unit 11 extracts user data corresponding to application IDs of target child applications among the user data stored in storage unit 12, and transmits them by including them in one transmission data. Furthermore, "a predetermined timing" means, for example, at 0:00, at 3:00 every Sunday, or at 3:00 at the end of the month, and is stored in storage unit 12 as a parameter. The user has the option of modifying the parameter using operation unit 14.

As described above, according to modification 1, plural applications in client terminal 10*a* can be managed, and processing of backup is executed in bulk by the parent application. Therefore, the user can save on communication cost because the number of times that communication takes place between client terminal 10*a* and backup server device 30 decreases. Furthermore, problems such as congestion are avoided, and management cost for the service provider can be reduced and the user can receive the service with greater reliability and ease, because the load of mobile communication network NW and Internet NET decreases. Furthermore, it can decrease the number of man-hours because the service provider should develop only the child applications to not have a backup function, therefore, it can reduce the cost of providing the service.

<Modification 2>

The user may be able to input the user data without downloading the application.

Figure 15:
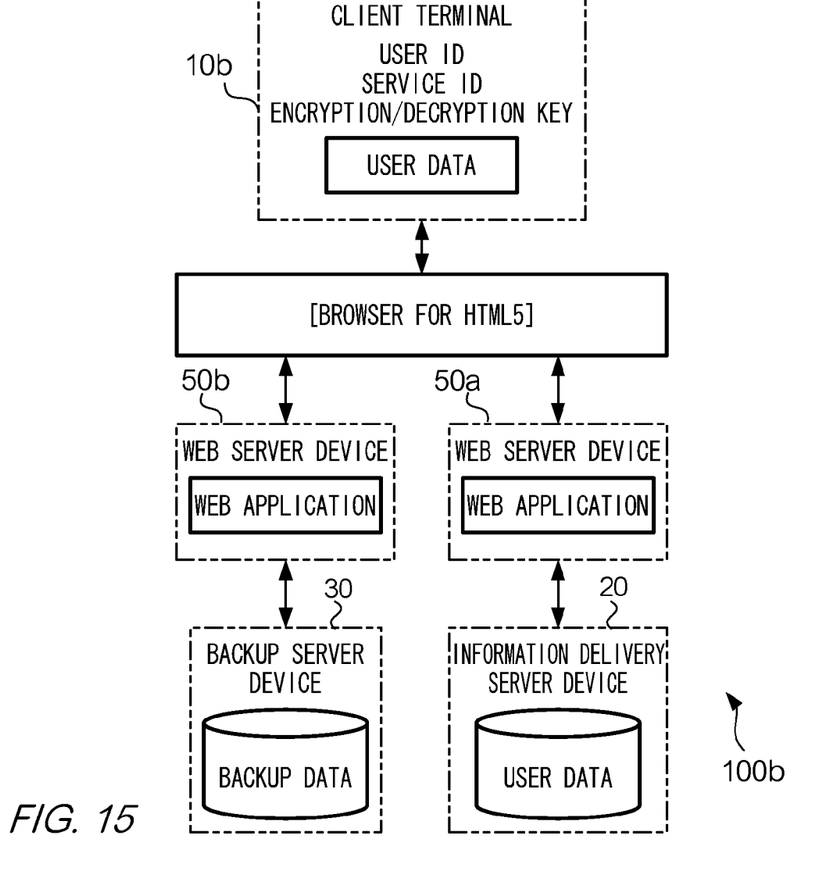
FIG. 15 is a pattern diagram schematically showing a configuration of a service-providing system of modification 2.

FIG. 15 is a pattern diagram schematically showing a configuration of service-providing system 100*b* according to modification 2. Service-providing system 100*b* is constructed by client terminal 10*b*, information delivery server device 20, backup server device 30, web server 50*a*, 50*b*, mobile communication network NW, Internet NET and advisory terminal 40. Mobile communication NW, Internet NET and advisory terminal 40 are the same as the ones shown in FIG. 1. Mobile communication network NW, Internet NET and advisory terminal 40 are the same as the ones described in modification 1. In the following description, web server 50*a* and 50*b* are referred to merely as web server 50 in a case that they are not distinguished from each other. In modification 2, the user does not use an application downloaded onto client terminal 10*b*, but uses a web browser corresponding to HTML (Hyper Text Markup Language) 5 for input of the user data. HTML5 is a markup language for accessing a web application through a site from a web browser and for use of the application. In the following description, the site for accessing the web application is called a service site. The service site is built, for example, in web server device 50. The web application is an application stored in web server device 50, and the user can use the web application through the service site by using a browser for HTML5. The user has downloaded and installed a browser for HTML5 onto client terminal 10*b* beforehand from the service site through mobile communication network NW and Internet NET. The user can use the web application stored in web server 50 without downloading the application onto client terminal 10*b*, by accessing the service site using the browser for HTML5.

Figure 16:
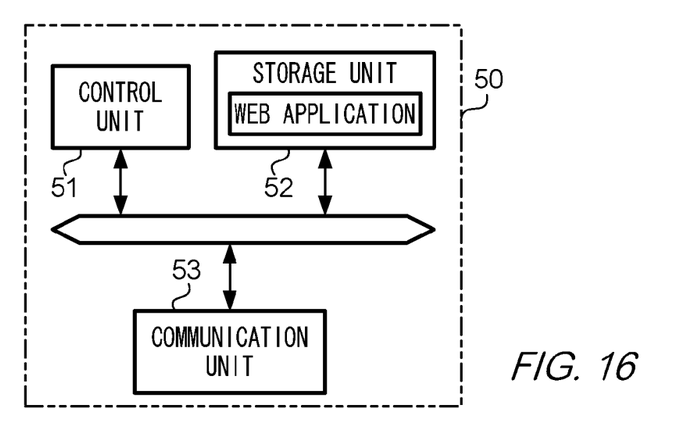
FIG. 16 is a block diagram showing a hardware configuration of a web server device.

FIG. 16 is a block diagram showing a hardware configuration of web server device 50. Web server device 50 includes control unit 51, storage unit 52 and communication unit 53, and the units are interconnected via a bus. Control unit 51 includes a CPU, a RAM and a ROM. CPU controls each unit of web server 50 by reading programs stored in ROM and/or storage unit 52, loading them onto the RAM and executing them. Storage unit 52 is a storage means such as a hard disk, and stores various programs, thresholds, and the web application. Communication unit 53 communicates with client terminal 10*b*, information delivery server device 20, backup server device 30 and advisory terminal 40 through network NW under the control of control unit 51.

In modification 2, the application according to service-providing system 100*b* is not downloaded onto client terminal 10*b*. Alternatively, application IDs similar to the ones of the embodiment are used as identifiers that identify each web application uniquely. If the user wants to use a particular web application from among web applications on the service site, first, an application ID is numbered. In this case, first, control unit 11 of client terminal 10*b* connects with the service site using communication unit 13 and the browser for HTML5, based on an instruction of a user who used operation unit 14. Then, upon the user instructing to begin use of a web application using operation unit 14, control unit 51 of web server device 50 numbers the application ID. Storage unit 52 of web server device 50 stores a numbered application ID table where numbered application IDs are stored, and control unit 51 numbers an ID that is not stored in the numbered application ID table as a new application ID, and stores the numbered application ID to storage unit 52 by adding the numbered application ID to the numbered application ID table. Then, control unit 51 transmits the numbered application ID in association with URLs of information delivery server device 20 and backup server device 30, being destination devices of the user data, to client terminal 10*b* using communication unit 53. Upon receiving the application ID using communication unit 13, control unit 11 of client terminal 10*b* lets storage unit 12 store the received application ID.

When inputting data, control unit 11 of client terminal 10*b*, at first, connects with the service site using communication unit 13, and the browser for HTML5 based on an instruction of the user who used operation unit 14. Then, a list of web applications that the user can use is displayed on the browser for HTML5. Upon the user appointing a web application that the user wants to use using operation unit 14, control unit 11 of client terminal 10*b* communicates with the web application by connecting with the service site using communication unit 13 by setting an application ID of the appointed web application as a parameter of the URLs. During the operation, the application ID of the web application is set as a parameter of a URL of information delivery server device 20 that is going to be communicated with and a URL of the service site, which are transmitted to web server 50*a* from client terminal 10*b*. Upon receiving the URLs using communication unit 53, control unit 51 of web server 50*a* transmits the application ID to information delivery server device 20 indicated by the received URL. Upon receiving the application ID using communication unit 23, control unit 21 of information delivery server device 20 performs certification by collating the received application with the numbered application ID table stored in storage unit 22. Control unit 21 of information delivery server device 20 transmits the result of the certification to client terminal 10*b* using communication unit 23. If the certification is completed successfully, control unit 11 of client terminal 10*b* encrypts the input user data by, for example, SSL. After that, control unit 11 transmits the user data encrypted by SSL in association with the application ID of child application A (application IDa) to web server device 50, and application IDa is set as a parameter of a URL of information server device 20 using communication unit 13. Upon receiving the data using communication unit 53, control unit 51 of web server device 50 transmits the received encrypted user data in association with application IDa to information delivery server device 20 indicated by the received URL. Upon receiving the encrypted user data using communication unit 23, control unit 21 of information delivery server device 20 decrypts the received user data by SSL. After that, control unit 21 lets storage unit 22 store the decrypted user data in association with the received application ID.

Control unit 11 performs certification for backup server device 30 using communication unit 13 and the certification information via web server device 50*b*. Specifically, control unit 11 transmits the certification and the URL of backup server device 30 to web server 50*b* using communication unit 13. Upon receiving the certification using communication unit 53, control unit 51 of web server device 50*b* transfers the certification information for backup server device 30 indicated by the received URL. Control unit 31 of backup server device 30 performs certification by collating the received certification information with the list of the certification stored in storage unit 32. Control unit 31 transmits a result of the certification to web server 50*b* using communication unit 33. Upon receiving the result of the certification using communication unit 53, control unit 51 of web server device 50*b* transfers the result of the certification for client terminal 10*b*. In the following description, a case that of the certification being completed successfully is described.

Upon the certification being completed successfully, control unit 11 encrypts the input user data using the encryption/decryption key. After that, control unit 11 transmits the encrypted user data in association with the user ID and an IP address of backup server device 30 to web server device 50*b* using communication unit 13. Upon receiving the encrypted user data and the user ID using communication unit 53, control unit 51 of web server device 50*b* transfers the encrypted user data in association with the received user ID for backup server device 30 indicated by the received IP address. Upon receiving the encrypted user data with the user ID using communication unit 33, control unit 31 of backup server device 30 lets storage unit 32 store the encrypted user data in association with the received user ID.

According to modification 2, the user has an advantage in that the user can save the trouble of downloading the application onto client terminal 10*b* that the user owns. Furthermore, the user can save communication cost relating to downloading. In addition, the cost of mobile communication network NW and Internet NET is kept low because communication for downloading does not occur, therefore, the service provider can control management cost. In addition, when another version of the web application occurs, the user can save the trouble of downloading the application again and the service provider can save the trouble of delivering the application again.

<Modification 3>

In a case that a user uses service-providing system 100 by using plural client terminals 10, plural client terminals 10 may synchronize the user data with each other. Modification 3 describes a case, for example, when the user uses two client terminals 10 such as a mobile phone and a home PC. In the present modification, the mobile phone is called client terminal 10X, and the PC is called client terminal 10Y. Furthermore, in the present modification, an application that the user uses is only the health management application. Moreover, in the present modification, an encryption/decryption key stored in client terminal 10X is equal to an encryption/decryption key stored in client terminal 10Y because the same user sets the key.

As the application ID is numbered with respect to each download, an application ID stored in client terminal 10X is different from an application ID stored in client terminal 10Y. User data input from client terminal 10X is stored in information delivery server device 20 without being associated with user data input from client terminal 10Y because user data is transmitted to information delivery server device 20 using application IDs. In other words, user data that can be referred to by client terminal 10X is different from user data that can be referred to by client terminal 10Y. On the other hand, user data input from client terminal 10X is stored in backup server device 30 in association with user data input from client terminal 10Y by a user ID because the encrypted user data transmitted to backup server device 30 is associated with the user ID.

In a case that the user wants both of the user data input by client terminal 10X and the user data input by client terminal 10Y to be able to be referred to by client terminal 10X or client terminal 10Y, synchronous processing of data is required.

Figure 17:
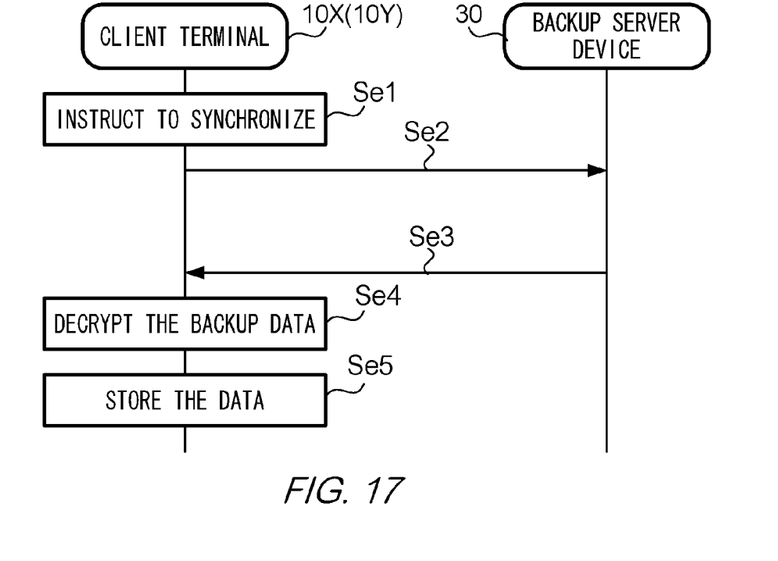
FIG. 17 is a sequence diagram showing synchronous processing of data.

FIG. 17 is a sequence diagram showing synchronous processing of data. In this case, first, the user instructs to synchronize data for client terminal 10X using operation unit 14, and control unit 11 accepts the instruction (step Se1). Next, control unit 11 of client terminal 10X transmits an instruction to synchronize including user ID to backup server device 30 using communication unit 13 (step Se2). Upon receiving the instruction using communication unit 33, control unit 31 of backup server device 30 transmits encrypted user data that corresponds to the received user ID to client terminal 10X using communication unit 33 (step Se3). Upon receiving the encrypted user data using communication unit 13, control unit 11 of client terminal 10X decrypts the received encrypted user data using the encryption/decryption key and lets storage unit 12 store the decrypted user data (step Se4). In this way, user data stored in client terminal 10X becomes combined with what the user data input by client terminal 10X and the data input by client terminal 10Y. In addition, client terminal 10Y executes a similar processing to that of the processing of client terminal 10X based on an operation of the user who used operation unit 14. It causes a condition whereby the user data stored in client terminal 10X and user data stored in client terminal 10Y are synchronized. After that, data in information delivery server device 20 will be synchronized according to the timing when data transmitting from client terminal 10X or client terminal 10Y to information delivery server device 20 occurs.

According to modification 3, the user can refer to user data input by all client terminals 10 that the user manages using any one of client terminals 10 in a case that the user uses one application with plural client terminals 10, therefore, the user can save the trouble of having to use client terminals 10 by referring to other clients terminals 10.

In the embodiment, an example when the service provider is a health club is described. However, the example is not only applicable to that described above, but also applicable to a medical information management system of hospitals, a supervised administration system, a dietary management system, and so on. In other words, it may also be applicable to a system where data input by a user, which includes personal information that is to be kept confidential, is protected such that the data is not identifiable by a third party when a service provider refers to the user data.

In the embodiment, the request of downloading the advice in step Sc6 is instructed by the user, however, the request may not be instructed manually. Control 11 may perform the processing at a predetermined timing. The predetermined timing is, for example, at 0:00, 3:00 etc. on each Sunday, and at 3:00 on the last day of each month, and may be stored in storage unit 12 as a parameter. The user has the option of modifying the parameter using operation unit 14.

<Modification 6>

When client terminal 10 transmits the user data to information delivery server device 20, the encryption by SSL is not required and other encryption methods may be used.

<Modification 7>

In the embodiment, the website for application delivery is built in backup server device 30; however, it may be built in information delivery server device 20, or other server devices.

<Modification 8>

The present invention may be understood as a program for causing a computer of client terminal 10 to realize the present invention or a recording medium such as an optical disk storing the program. The program according to the present invention may be provided by being downloaded onto client terminal 10 via a network such as the Internet and installed, so as to be available to a user.

What is claimed is:

1. An information-processing device comprising:
    a user data set obtaining unit that obtains a user data set associated with a user, the user data set not including information identifying the user personally;
    a user identifier obtaining unit that obtains a user identifier assigned to the user uniquely;
    an application identifier obtaining unit that obtains an application identifier identifying an application program indicating a procedure for providing a service to the user based on the user data set, the application identifier being assigned to the application program so that each application program executed in each information-processing device is uniquely identified by the application identifier;
    a first processing unit that transmits the user data set obtained by the user data set obtaining unit when the application program is executed and transmits the application identifier assigned to the application program executed in the information-processing device to a first server device providing the service to the user based on the user data set, receives service information associated with the service from the first server device, and outputs the service information; and
    a second processing unit that encrypts the user data set and transmits the encrypted user data set and the user identifier obtained by the user identifier obtaining unit to a device different from the first server device, the device certifying the user with the user identifier transmitted by the second processing unit, and after the user is certified by the device, the device numbers an application identifier and transmits the application identifier to the first processing unit, the first processing unit transmits the application identifier and the user data set to the first server device.

2. The information-processing device according to claim 1, wherein:
    the second processing unit transmits a request for the encrypted user data set to the device different from the first server device, receives the encrypted user data set transmitted from the device in response to the request, and decrypts the received encrypted user data set.

3. The information-processing device according to claim 1, wherein:
    when a plurality of services are provided by one or a plurality of first server devices,
    the first processing unit, in connection with each of said one or the plurality of first server devices providing each of the plurality of services, transmits to the first server device the user data set obtained when the application program indicating the procedure for providing the service to the user is executed and the application identifier assigned to the application program is executed in the information-processing device, and receives the service information associated with the service from the first server device; and
    the second processing unit encrypts each of user data sets obtained by the user data obtaining unit when each of a plurality of application programs for providing each of the plurality of services is executed, and transmits all of the encrypted user data sets at once in association with the user identifier.

4. The information-processing device according to claim 1, wherein:
    each of the application programs is stored in the first server device,
    the application identifier obtaining unit obtains the application identifier uniquely assigned to an application program executed in the information-processing device from the first server device by use of a web browser compliant with Hyper Text Mark-up Language 5 (HTML5), and
    the first processing unit and the second processing unit carry out data communication with the first server device and the device by use of the web browser.

5. A service-providing system comprising:
    a plurality of information-processing devices;
    an input terminal;
    a first server device that provides a service to a user based on a user data set associated with the user, the user data set not including information identifying the user personally; and
    a device different from the first server device that stores the user data set encrypted in association with a user identifier assigned to the user; wherein
    each information-processing device comprising:
    a user data set obtaining unit that obtains a user data set associated with a user of the information-processing device, the user data set not including information identifying the user of the information-processing device personally;

a user identifier obtaining unit that obtains a user identifier assigned to the user uniquely;

an application identifier obtaining unit that obtains an application identifier to identify an application program indicating a procedure for providing a service to the user based on the user data set, the application identifier being assigned to the application program so that each application program executed in each information-processing device is uniquely identified by the application identifier;

a first processing unit that transmits, when the application program is executed, the user data set obtained by the user data set obtaining unit and the application identifier assigned to the application program executed in the information-processing device to the first server device, and receives service information associated with the service from the first server device, and outputs the service information; and a second processing unit that encrypts the user data set and transmits the encrypted user data set and the user identifier obtained by the user identifier obtaining unit to the device different from the first server, the device certifying the user with the user identifier transmitted by the second processing unit, and after the user is certified by the device, the device numbers an application identifier and transmits the application identifier to the first processing unit, the first processing unit transmits the application identifier and the user data set to the first server, the second processing unit further requests the encrypted user data set from the device, receives the encrypted user data set transmitted from the device in response to the request, and decrypts the received encrypted data set;

the input terminal comprising:
a display unit that displays the user data set stored in the first server device; and
an operation unit that accepts an operation to input the service information and the application identifier;

the first server device comprising:
a first receiving unit that receives the user data set and the application identifier from the information-processing device;
a first storage unit that stores the user data set received by the first receiving unit in association with the application identifier, and stores the service information input at the input device in association with the user data set corresponding to the application identifier input at the input device; and
a first transmission unit that transmits the service information to the information-processing device;

the device comprising:
a second receiving unit that receives the encrypted user data set and the user identifier from the information-processing device; and
a second storage unit that stores the encrypted user data set in association with the user identifier received by the second receiving unit.

6. A service providing method comprising:
a step of obtaining a user data set associated with a user, the user data set not including information identifying the user personally;
a step of obtaining a user identifier assigned to the user uniquely;
a step of obtaining an application identifier to identify an application program indicating a procedure for providing a service to the user based on the user data set, the application identifier being assigned to the application program so that each application program executed in each information-processing device is uniquely identified by the application identifier;
a step of transmitting the user data set obtained when the application program is executed and the application identifier assigned to the application program executed in the information-processing device to a first server device providing the service to the user based on the user data set, receiving service information associated with the service from the first server device, and outputting the service information;
a step of encrypting the user data set; and
a step of transmitting the encrypted user data set and the obtained user identifier to a device different from the first server device, the device certifying the user with the transmitted user identifier, and after the user is certified by the device, the device numbers an application identifier and transmits the application identifier to the information processing device, the information processing device transmits the application identifier and the user data set to the first server device.

7. A program stored on a non-transitory storage medium, the program causing a computer to execute:
a step of obtaining a user data set associated with a user, the user data set not including information identifying the user personally;
a step of obtaining a user identifier assigned to the user uniquely;
a step of obtaining an application identifier to identify an application program indicating a procedure for providing a service to the user based on the user data set, the application identifier being assigned to the application program so that each application program executed in each information-processing device is uniquely identified by the application identifier;
a step of transmitting the user data set obtained when the application program is executed and the application identifier assigned to the application program executed in the information-processing device to a first server device providing the service to the user based on the user data set, receiving service information associated with the service from the first server device, and outputting the service information;
a step of encrypting the user data set; and
a step of transmitting the encrypted user data set and the obtained user identifier to a device different from the first server device, the device certifying the user with the transmitted user identifier, and after the user is certified by the device, the device numbers an application identifier and transmits the application identifier to an information-processing device, the information-processing device transmits the application identifier and the user data set to the first server device.

* * * * *